United States Patent
Pyun

(10) Patent No.: US 12,097,247 B2
(45) Date of Patent: Sep. 24, 2024

(54) PHARMACEUTICAL COMPOSITION AND KIT FOR TREATING GOUT

(71) Applicant: UNIVERSITY-INDUSTRY FOUNDATION(UIF), YONSEI UNIVERSITY, Seoul (KR)

(72) Inventor: Jae-Chul Pyun, Seoul (KR)

(73) Assignee: UNIVERSITY-INDUSTRY FOUNDATION(UIF), YONSEI UNIVERSITY, Seoul (KR)

(*) Notice: Subject to any disclaimer, the term of this patent is extended or adjusted under 35 U.S.C. 154(b) by 0 days.

(21) Appl. No.: 16/996,846

(22) Filed: Aug. 18, 2020

(65) Prior Publication Data
US 2024/0066107 A1 Feb. 29, 2024

(30) Foreign Application Priority Data
Aug. 19, 2019 (KR) .......... 10-2019-0101415

(51) Int. Cl.
- *A61K 47/64* (2017.01)
- *A61K 38/44* (2006.01)
- *A61K 38/50* (2006.01)
- *G01N 33/68* (2006.01)

(52) U.S. Cl.
CPC .............. *A61K 38/50* (2013.01); *A61K 38/44* (2013.01); *G01N 33/6848* (2013.01)

(58) Field of Classification Search
CPC ..... A61K 38/50; A61K 38/44; G01N 33/6848
See application file for complete search history.

(56) References Cited

U.S. PATENT DOCUMENTS

2010/0160351 A1 * 6/2010 Jenkins .................. A61K 45/06

FOREIGN PATENT DOCUMENTS

| KR | 10-1702897 | | 2/2017 |
|---|---|---|---|
| WO | WO2009120707 A1 | * | 10/2009 |
| WO | WO2011025964 A2 | * | 3/2011 |
| WO | WO2011051327 A2 | * | 5/2011 |
| WO | WO2011083140 A1 | * | 7/2011 |
| WO | WO2017122019 A1 | * | 7/2011 |
| WO | WO2015042204 A1 | * | 3/2015 |
| WO | 2016/116907 | | 7/2016 |
| WO | WO2017156270 A1 | * | 9/2017 |

OTHER PUBLICATIONS

Tiwari et al., Urate crystal degradation for treatment of gout: a nanoparticulate combination therapy approach, Drug Delivery and Translational Research, 2015, 5:219-230 (Year: 2015).*

* cited by examiner

*Primary Examiner* — James H Alstrum-Acevedo
*Assistant Examiner* — Saleha Kuzniewski
(74) *Attorney, Agent, or Firm* — NSIP Law

(57) ABSTRACT

The present invention relates to a pharmaceutical composition for treating gout and a gout treatment kit. According to an embodiment of the present invention, a pharmaceutical composition for treating gout comprising a probe containing at least one or more peptides specifically coupled to a monosodium urate (MSU) crystals and a first enzyme which is coupled to the probe and reacts with the target MSU crystal coupled to the probe or urea of surrounding joint fluid to remove the target MSU crystal is provided.

17 Claims, 7 Drawing Sheets
Specification includes a Sequence Listing.

PHARMACEUTICAL COMPOSITION AND KIT FOR TREATING GOUT

CROSS-REFERENCE TO RELATED APPLICATION

The present application claims the benefit of Korean Application No. 10-2019-00101415, filed on Aug. 19, 2019, which is incorporated herein by reference in its entirety.

SEQUENCE LISTING

This instant application contains a Sequence Listing which has been submitted electronically in ASCII format and is hereby incorporated by reference in its entirety. Said ASCII copy, created on Aug. 6, 2020, is named Substitute-SQ-listing.text and is 1414 bits in size.

BACKGROUND OF THE INVENTION

1. Field

The present invention relates to a bio-composition, and more particularly, to a pharmaceutical composition and kit for treating gout.

2. Description of the Related Art

The cause of gout is an inflammation caused by the immune response of the living body to the needle-shaped crystals generated in a patient's joint. The inflammation causes pain in the area where the joint is located. The needle-shaped crystals are monosodium urate (MSU) crystals, and the MSU crystals are generated, when urea as a product of purine nucleotide in the body are excessively generated and the urea cannot be properly discharged outside the body, and then the urea is saturated, and accordingly, is crystalized.

When the immune system causes an immune response to the MSU crystal, an acute gout attack or complication disease may be induced, and thus, proper treatment of gout is important. In addition, the number of the gout patients all over the world is increasing rapidly, and in particular, the incidence rate of the gout is higher than that of rheumatoid arthritis in the United States.

As a conventional gout treatment, a method of lowering the urea concentration in blood by improving lifestyle when measuring the urea concentration in blood, and as a result, it exceeds 7.0 mL/dL; and a method for administering a pain reliever for joint syringe injection or administering an anti-inflammatory agent when the MSU crystal trespasses into the joint and, therefore, an acute seizure begins has been used. However, the method of improving lifestyle takes a long time, and it is nearly impossible to expect a dramatic effect to treat the acute gout, and the method for administering the pain reliever or the anti-inflammatory agent may not be a fundamental solution for treating gout.

Therefore, there is a need for a treatment that has an effect of calming the gout attacks and may fundamentally eliminate the cause of gout. To this end, it is preferable to solve the cause of the gout attack by directly removing the MSU crystal.

SUMMARY OF THE INVENTION

The problem to be solved by the present invention is to provide a pharmaceutical composition for treating gout which removes MSU crystals which are the basic cause of gout attacks as a fundamental solution, and not as a temporary solution such as a pain reliever or an anti-inflammatory agent.

Another problem to be solved by the present invention is to provide a pharmaceutical composition for treating gout, which has the above-described advantages, does not have side effects such as immune rejection reaction or inflammatory reaction, and can be continuously administered even in vivo.

Another problem to be solved by the present invention is to provide a gout treatment kit which has the above-described advantages, is easily available, has high accessibility, and may be commercialized.

A pharmaceutical composition for treating gout according to an embodiment of the present invention for solving the above problems may comprise a probe containing at least one or more peptides specifically coupling to monosodium urate MSU crystals; and a first enzyme which is coupled to the probe and reacts with the target MSU crystal coupled to the probe or urea of the surrounding joint fluid to remove the target MSU crystal. In another embodiment, the peptide may include at least one or more of the peptides having the sequence of SEQ ID NO: 1 to SEQ ID NO: 5.

In one embodiment, the first enzyme may generate ammonium ions in the surrounding joint fluid to raise the pH of the surrounding joint fluid, thereby dissolving and removing the target MSU crystal. In another embodiment, the first enzyme oxidize the target MSU crystal coupled to the probe or the urea of the surrounding joint fluid to decompose and remove the target MSU crystal. In another embodiment, the first enzyme may include at least one or more of uricase, rasburicase, or urease, and optionally, the first enzyme may be selected from human-derived substances so as not to cause an immune rejection reaction in a human body.

The pharmaceutical composition for treating gout according to an embodiment of the present invention may further include a linker coupled between the probe and the first enzyme to provide a predetermined degree of freedom to the probe. In another embodiment, the pharmaceutical composition for treating gout may further include a second enzyme which removes an occupying protein adsorbed on the target MSU crystal.

In one embodiment, it may further include a biodegradable support for carrying a cluster of a unit composition formed by combining the first enzyme and the probe, and is maintained as a limited level for a predetermined period in vivo. In another embodiment, the pharmaceutical composition for treating gout may further include a second enzyme which removes an occupying protein adsorbed on the target MSU crystal, and the biodegradable support may contain the second enzyme.

The pharmaceutical composition for treating gout according to another embodiment of the present invention for solving the above problems may comprise a support, a probe including at least one or more peptides which are coupled to and fixed to a portion of the support, and specifically coupled to monosodium urate MSU crystals, and a first enzyme which is coupled to and fixed to another portion of the support, and reacts with a target MSU crystal coupled to the probe or an element of the surrounding joint fluid to remove the target MSU crystal. In another embodiment, a linker coupled between the support and the probe may be further included to provide a predetermined degree of freedom to the probe. In another embodiment, the support may inhibit structural variation of the probe or the first enzyme.

In one embodiment, the first enzyme may generate ammonium ions in the surrounding joint fluid to raise the pH of the surrounding joint fluid, thereby dissolving and removing the target MSU crystal. In another embodiment, the first enzyme may decompose and remove the target MSU crystal by oxidizing the urea of the target MSU crystal coupled to the probe or the surrounding joint fluid. In another embodiment, the first enzyme may include at least one or more of uricase, rasburicase, and urease.

In one embodiment, the support may be any one of a fully particulated structure, a porous structure, a chain structure, a network structure, a plate structure, a linear structure, or a combination thereof, and in another embodiment, the support may include one or more of biocompatible inorganic substance, collagen, hyaluronic acid, chitosan, gelatin, polysaccharides, polylactic acid (PLA), or polyglycolide (PGA). In another embodiment, the pharmaceutical composition for treating gout may further include a decomposition accelerator for increasing the biodegradation rate of the support or a decomposition retarding agent for reducing the biodegradation rate of the support, and in another embodiment, the support may include a color developing substance, a light emitting substance, a fluorescent substance, or a combination thereof.

In one embodiment, the pharmaceutical composition for treating gout may further include a second enzyme which removes an occupying protein adsorbed on the target MSU crystal, and in another embodiment, the pharmaceutical composition for treating gout may further include a third enzyme which decomposes the protein in the joint fluid containing the target MSU crystal.

A gout treatment kit according to an another embodiment of the present invention for solving the above problems may include a pharmaceutical composition comprising a probe containing at least one or more peptides selectively reacting with monosodium urate MSU crystals; and a first enzyme which is coupled to the probe and reacts with the target MSU crystal coupled to the probe or urea of the surrounding joint fluid to remove the target MSU crystal. In another embodiment, the gout treatment kit may further comprise a gout diagnosis probe and a secondary expression substrate, and the gout diagnosis probe may comprise a peptide coupled to at least one or more labeling substances or at least one or more first expression substrates. The labeling substance may cause at least one or more of optical change, electrical change, or chemical change of the secondary expression substrate by a catalytic reaction. The first or secondary expression substrates may include a color developing substance, a light emitting substance, a fluorescent substance, or a combination thereof, and the peptide may include at least one or more of the amino acids of sequence of SEQ ID NO: 1 to 5. In another embodiment, the kit for treatment of gout further comprises a sample plate for mass spectrometry. The sample plate includes the matrix layer 322 formed by any one of a nanoparticle structure containing $TiO_2$, a nanowire structure containing $TiO_2$, and a composite nanostructure coated with $TiO_2$ nanoparticles on the nanowire containing $TiO_2$.

According to an embodiment of the present invention, the MSU crystal may be effectively removed with a small amount of the composition by combining a probe containing a peptide that is specifically coupled to the MSU crystal causing gout, and a first enzyme which dissolves the MSU crystal. In addition, a pharmaceutical composition for treating gout can dissolve only the MSU crystals without damaging other proteins in a living body, since the first enzymes are intensively disposed around the MSU crystals.

According to another embodiment of the present invention, since the probe and the first enzyme are combined with a support and are fixed by the support, the probe and the first enzyme may maintain the 3-dimensional protein structure as it is, in spite of environmental changes in temperature or pH around the first enzyme. Therefore, the original function of the first enzyme is maintained without being deteriorated, and a pharmaceutical composition for treating gout with high efficiency may be provided.

In addition, according to another embodiment of the present invention, a kit for treating gout may be provided which may easily apply the pharmaceutical composition for treating gout having the above-described advantages to the treatment of gout.

DETAILED DESCRIPTION OF THE INVENTION

Figure 1:
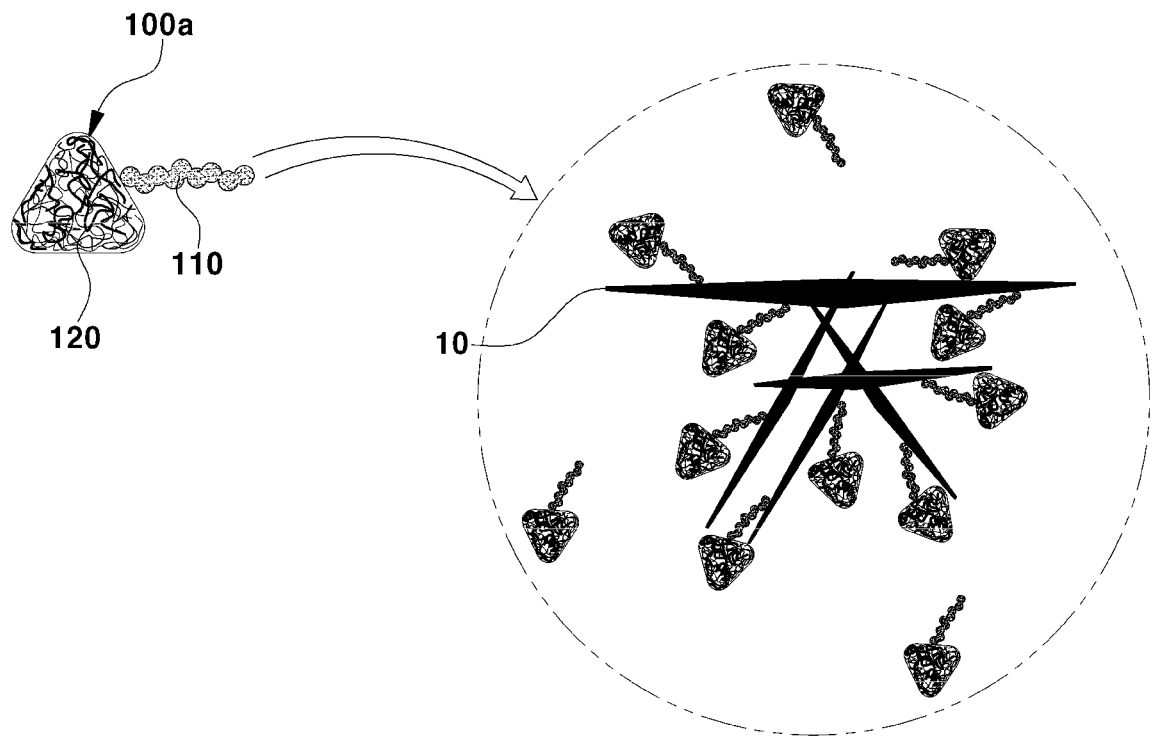
FIG. 1 is a diagram showing a pharmaceutical composition for treating gout and a monosodium urate MSU crystal according to an embodiment of the present invention.

In the following, the embodiments of the present invention will be described with reference to cross-sectional diagrams schematically showing deal embodiments (and intermediate structures) of the present invention. In these drawings, for example, the size and the shape of the members may be exaggerated for convenience and clarity of description, and in actual implementation, changes of the illustrated shape may be expected. Accordingly, the embodiments of the present invention should not be construed as limited to the specific shapes of the regions shown herein. In addition, the reference numerals of the members in the drawings refer to the same members throughout the drawings.

Hereinafter, preferred embodiments of the present invention will be described in detail with reference to the accompanying drawings.

The embodiments of the present invention are provided to more completely describe the present invention to those having a common knowledge in a related art, and the following examples may be modified in various other forms. Further, the scope of the present invention is not limited to the following embodiments. Rather, these embodiments are provided to make the present descriptions more faithful and complete, and to completely convey the spirit of the present invention to those skilled in the art.

In the drawings, the same reference numerals refer to the same elements. Also, as used herein, the term, "and/or" includes any one of the corresponding listed items, and all combinations of one or more items The terminology used herein is used to describe a specific embodiment and is not intended to limit the present invention. As used herein, a singular form may include plural forms unless the context clearly indicates otherwise. Also, as used herein, the term such as "comprise" and/or "comprising" specifies the mentioned shapes, numbers, steps, actions, members, elements and/or the presence of these groups, and does not exclude the presence or addition of one or more other shapes, numbers, actions, members, elements and/or presence or addition of groups.

Reference to a layer formed "on" a substrate or other layer herein refers to a layer formed directly on the substrate or other layer; or also may refer to an intermediate layer formed on the substrate or other layer, or a layer formed on intermediate layers. Further, for those skilled in the art, a structure or shape arranged "adjacent" to another shape may have a portion disposed below or overlapping the adjacent shape.

In this specification, as shown on the drawings, the relative terms such as "below", "above", "upper", "lower", "horizontal" or "vertical" may be used to describe the relationship between one component member, one layer, or one region and another component member, another layer, or another region. It is to be understood that these terms encompass not only the orientation indicated in the figures, but also other orientations of the device.

FIG. 1 is a diagram showing a pharmaceutical composition 100a for treating gout and a monosodium urate MSU crystal 10 according to an embodiment of the present invention.

Referring to FIG. 1, in an embodiment, the pharmaceutical composition 100a for treating gout treatment may include a probe 110 including a peptide, and a first enzyme 120 coupled to the probe 110. The peptide may be a polymer of amino acids which specifically coupled to MSU crystals. In one embodiment, the probe 110 may include at least one or more of peptides having a sequence of SEQ ID NO: 1 to SEQ ID NO: 5 capable of specifically coupling to MSU crystals.

In one embodiment, the peptide may include peptide 1: ARGVNPGIMGRDYWG (SEQ ID NO: 1), peptide 2: ARYAGSLESGADDWG (SEQ ID NO: 2), peptide 3: ARCESGRPGSVDFWG (SEQ ID NO: 3), peptide 4: ARCLELLGRKIDFWG (SEQ ID NO: 4) and peptide 5: ARCVDGISRLRDDWG (SEQ ID NO: 5). Among the sequences of SEQ ID NOs: 1 to 5, 11 amino acids may have a selective reactivity to monosodium urate MSU, except for the amino acid sequence consisting of the first AR and the last WG. The peptides 1 to 5 may be artificially synthesized through a peptide library or an amino acid library of a commercial organization or public institution.

In another embodiment, a peptide may be included in which a plurality of sequences among the sequences of SEQ ID NOs: 1 to 5 are coupled continuously. The peptide may be a peptide having 15 amino acids, 30 amino acids, and 45 amino acids, and may be a polymer formed by polymerization of the peptides. Alternatively, it may be a peptide having a plurality of the amino acid sequences, that is, the 11 amino acid sequence having selective reactivity with MSU crystals among the sequences of SEQ ID NOs: 1 to 5, and having amino acids of AR and WG at the start and end portions, respectively.

The peptide of the probe 110 may be coupled by MSU crystal and a host-guest reaction, or specifically or selectively coupled by an antigen-antibody reaction. Various types of proteins or peptides may be included in the joint fluid of a patient in which the MSU crystal is present. However, since the probe 110 is specifically or selectively combined with the MSU crystal, the action of the first enzyme 120 is locally performed to the MSU so as not to destroy substances such as other biological proteins in the joint fluid, and thus, MSU crystals may be selectively removed. This is because the probe 110 has a specific coupling property with the MSU crystal, so that the first enzyme 120 may move near the target MSU crystal 10 in a state in which the first enzyme 120 is coupled with the probe 110.

The first enzyme 120 moved to the target MSU crystal 10 may react with the target MSU crystal 10 itself or the elements of the joint fluid around the target MSU crystal 10 (hereinafter, referred to as surrounding joint fluid). Since the first enzyme 120 selectively reacts on the target MSU crystal 10 by the probe 110, even if only a small amount of the first enzyme 120 is administered, the pharmaceutical effect that the pharmacological composition may effectively calm gout attacks may be obtained. As a result, while the first enzyme 120 reacts efficiently, thereby minimizing side effects due to an immune reaction in the human body by the first enzyme 120, the treatment on the gout may be possible.

In one embodiment, the first enzyme 120 may include at least one or more among uricase, rasburicase, and urease. The uricase or the rasburicase may oxidize urea to produce allantoin. The uricase may be obtained from a mouse. In another embodiment, the first enzyme 120 may be selected from human-derived substances so as not to cause an immune rejection reaction in the human body. For example, the first enzyme 120 may be urease. The above-described substances are only non-limiting examples, and all kinds of known techniques related to substances such as compounds, enzymes or catalysts capable of decomposing MSU crystals may be referred for the first enzyme 120.

In one embodiment, the first enzyme 120 may include urease. Urease may increase the pH of the joint fluid around urease by reacting with the target MSU crystal 10 or urea of the surrounding joint fluid to generate ammonium ions. When the probe 110 coupled with the first enzyme 120 is combined with the target MSU crystal 10, the pH of the joint fluid around the target MSU crystal 10 may increase, and accordingly, the target MSU crystal 10 may be dissolved and removed. The pH of the surrounding joint fluid may be in the range of 8 to 12. When the pH is less than 8, the target MSU crystal 10 is not sufficiently dissolved and there is a risk of gout attacks, and when the pH exceeds 12, the three-dimensional structure of other bio substances inside the joint fluid may be destroyed and thus, it is not desirable. In particular, in the case of using urease for a human for the purpose of gout treatment, there is an advantage as follows. That is, since urease is an enzyme present in a human body, even if it is administered into the human body, it does not cause an immune rejection reaction, and thus, it may be safely administered to the human body several times. Therefore, the concentration of urea in the blood rises to generate MSU crystals, and a treatment is carried out by administering a pharmaceutical composition 100, 200 for treating gout in order to remove the MSU crystals. After several months or years, when the concentration of urea in the blood rises again, and even if MSU crystals are regenerated, the pharmaceutical compositions 100, 200 for treating gout may be re-administered. In addition, a pharmaceutical composition for treating gout in which an immune rejection reaction does not occur may be provided to patients having a consistently high urea concentration in blood even if continuously administered every several weeks to several months for the patients.

In an embodiment, urea may be provided together to accelerate the reaction rate of the first enzyme 120. When the urea is provided together with the pharmaceutical composition 100, 200 for treating gout, the first enzyme 120 reacts with the urea at a high rate, so that the pH of the joint fluid around the target MSU crystal 10 may increase at a very high speed. In particular, when the first enzyme 120 is urease, the increasing rate of the pH is increased, so that the MSU crystal may be rapidly dissolved.

In one embodiment, the first enzyme 120 and the probe 110 may be coupled by a covalent bond. The first enzyme 120 and the probe 110 may be treated with EDC (1-ethyl-3-(3-dimethylaminopropyl)carbodiimide hydrochloride) and NHS (Sulfo-NHS (N-hydroxysulfosuccinimide)) to form a covalent bond. Alternatively, a covalent bond may be formed by treating the first enzyme 120 and the probe 110 with glutaraldehyde.

In another embodiment, the first enzyme 120 and the probe 110 may be combined by various physical or chemical bonds. The bond may be an ionic bond, a hydrogen bond or a host-guest bond. The above-described examples do not limit the present invention, and all kinds of known combinations may be applied.

Figure 2:
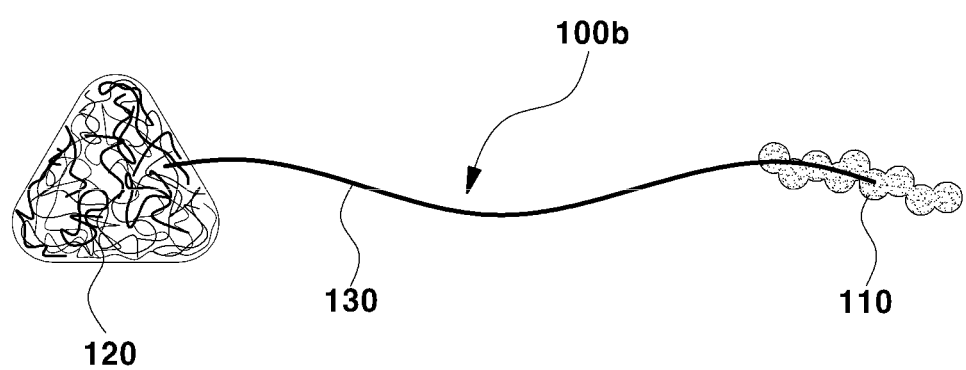
FIG. 2 is a diagram showing a pharmaceutical composition for treating gout according to another embodiment of the present invention.

FIG. 2 is a diagram showing a pharmaceutical composition 100b for treating gout according to another embodiment of the present invention.

Referring to FIG. 2, in one embodiment, the pharmaceutical composition 100b for treating gout may further include a linker 130 for providing a predetermined degree of freedom to the probe 110, and the first enzyme 120 and the probe 110 may be coupled by a linker 130. In general, the MSU crystal may have a size of several tens of μm, while the probe 110 may have a size of several tens of Å. When the size of the probe 110 is relatively small compared to the MSU crystal or the size of the first enzyme 120, the distance at which the probe 110 may move around the first enzyme 120 is limited. Thus, it may be difficult for the probe 110 to detect the MSU crystal and to be properly coupled to it. According to an embodiment of the present invention, since the first enzyme 120 and the probe 110 are connected via the linker 130, the degree of freedom in which the probe 110 may move around the first enzyme 120 may be increased.

In one embodiment, both ends of the linker 130 may contain the same or different chemical functional groups. The chemical functional group may include a carboxyl group, an amine group, an azide, a succinyl group, a thiol group, or a halogen. The linker 130 may have one end coupled to the first enzyme 120 and the other end coupled to the probe 110 by the chemical functional group In another embodiment, the first enzyme 120 and the linker 130 and/or the probe 110 and the linker 130 may be coupled by various chemical bonds. The chemical bond may be an ionic bond, a hydrogen bond or a host-guest bond. The above-described examples do not limit the present invention, and all kinds of known combinations may be applied.

In one embodiment, the linker 130 may be a molecule having a chain structure. For example, the chain structure may include a carbon chain in at least some part, and an amino acid, nucleic acid or sugar chain in at least some part. The total length of the linker 130 may be a length corresponding to the length of the carbon chain composed of several to hundreds of carbons. Alternatively, a single amino acid such as glycine G may be sequentially arranged. Optionally, glycine, serine or a combination thereof may be a repeated amino acid structure. This is a non-limiting example, and reference may be made to known techniques for all kinds of chemical reactions capable of forming bonds between enzymes and peptides.

In one embodiment, a plurality of probes 110 may be coupled to one first enzyme 120. The number of probes 110 coupled to the first enzyme 120 may vary depending on the type of coupling between the probe 110 and the first enzyme 120, and the number of a chemical function capable of performing the coupling present in the first enzyme 120. For example, as the number of the chemical functional group is increasing, much more probes 110 may be coupled. When the first enzyme 120 is coupled to the probe 110 by the linker 130, the number of coupling vary depending on the type of bond between the first enzyme 120 and the linker 130, and the number of chemical functional groups capable of such coupling. According to an embodiment of the present invention, unlike the case where the first enzyme 120 moves to the vicinity of the MSU crystal by a single probe 110, the searching for the MSU crystal by a plurality of probes 110 may increase the possibility that the enzyme 120 exists around the MSU crystal. Accordingly, even if the first enzyme 120 reacts with the target MSU crystal 10 or the urea of the surrounding joint fluid, there is no side effect since it does not affect other proteins in the body except for the MSU crystal, and it is possible to treat the gout with high efficiency with a small amount of the pharmaceutical composition.

In one embodiment, the pharmaceutical composition 100, 200 for treating gout may further include a second enzyme (150 in FIG. 3) which removes the occupying protein adsorbed on the target MSU crystal 10. Various types of proteins are present in the joint fluid of a patient with the gout, and some of the proteins may be adsorbed on MSU crystals to constitute the occupying protein. When the occupying protein is present on the target MSU crystal 10, the target MSU crystal 10 may be difficult to react with the first enzyme 120, and even if the first enzyme 120 reacts with the urea of the surrounding joint fluid containing the target MSU crystal 10 or the target MSU crystal 10 to increase the pH around the target MSU crystal 10, the target MSU crystal 10 may not dissolve easily. The occupying protein may include immunoglobulin G (IgG), immunoglobulin M (IgM), immunoglobulin A (IgA), C3, fibrinogen or albumin, and mainly IgG may be adsorbed in large amounts on the target MSU crystal 10. Accordingly, the pharmaceutical composition for treating gout may further include the second enzyme 150 for removing the occupying protein. In one embodiment, the second enzyme 150 may include protease K as an unlimiting example.

Figure 3:
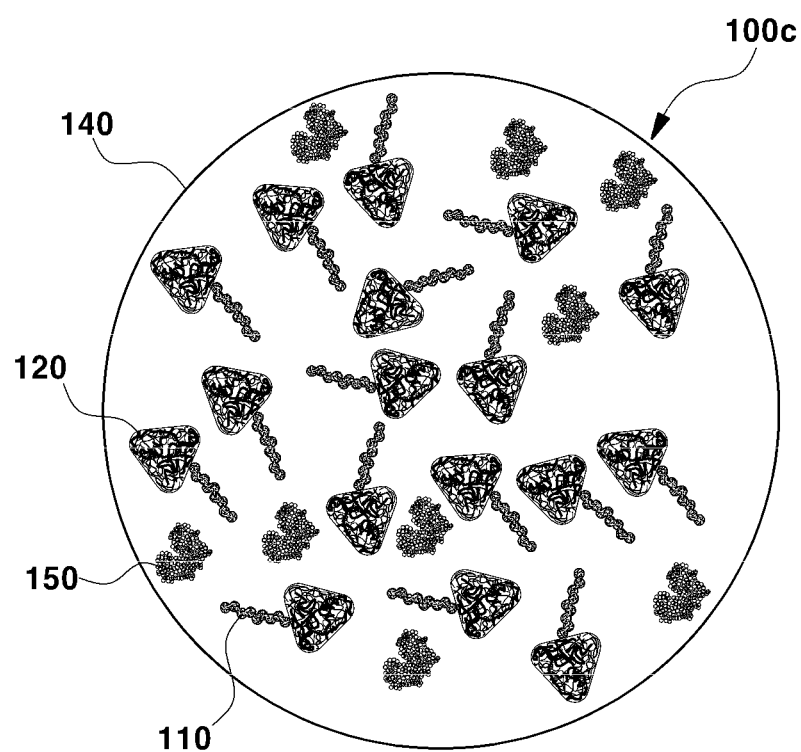
FIG. 3 is a diagram showing a pharmaceutical composition for treating gout according to another embodiment of the present invention.

FIG. 3 is a diagram showing a pharmaceutical composition 100c for treating gout according to another embodiment of the present invention.

Referring to FIG. 3, in one embodiment, the pharmaceutical composition 100c for treating gout may further include a biodegradable support 140 supporting a cluster of unit compositions formed by combining the first enzyme 120 and the probe 110. In FIG. 3, only a unit composition in which the first enzyme 120 and the probe 110 are directly coupled with each other is shown, but the unit composition may be one in which a first enzyme 120 and the probe 110 are directly coupled with each other, or may be one in which a first enzyme 120 and the probe 110 are coupled through the linker 130 therebetween. The biodegradable support 140 may be a capsule form, a gel form having a fluid form, or a substance having a porous structure. A cluster of unit compositions may be accommodated in the biodegradable support 140. The cluster may be meant to include a plurality of the unit compositions, and is not limited to a specific number. According to an embodiment of the present invention, the biodegradable support 140 may extend the maintenance time of the unit composition by protecting the unit composition from an external environment such as temperature or pH.

In one embodiment, the biodegradable support 140 may maintain limitedly the unit composition for a predetermined period of time. The predetermined period of time may be, for example, several weeks to several months. When the predetermined period of time is less than the threshold lower limit, the MSU crystal may not be sufficiently dissolved. In addition, when the biodegradable support 140 is not decomposed in vivo after the predetermined period and the unit composition continues to remain, side effects due to immune rejection or inflammatory reactions may occur.

In one embodiment, the second enzyme 150 may be accommodated in the biodegradable support 140 together with the unit composition. The biodegradable support 140 may include any one of biocompatible inorganic substances, collagen, hyaluronic acid, chitosan, gelatin, polysaccharides, polylactic acid (PLA), or polyglycolide JPGA). In another embodiment, an ionic lipid body may be used. Alternatively, the biodegradable support 140 may include polyacrylic acid (PAA). In other example, the unit composition and/or the second enzyme 150 may be included in a micelle by forming the micelle using a block copolymerized polymer, FIG. 4A is a diagram showing a pharmaceutical composition 200a for treating gout according to an embodiment of the present invention, FIG. 4B is a diagram showing a pharmaceutical composition 200b for treating gout according to another embodiment of the present invention, FIG. 4C is a diagram showing a pharmaceutical composition 200c for treating gout according to another embodiment of the present invention, and FIG. 4D is a cross-sectional diagram of the pharmaceutical composition 200d for treating gout according to another embodiment of the present invention.

Figure 4A:
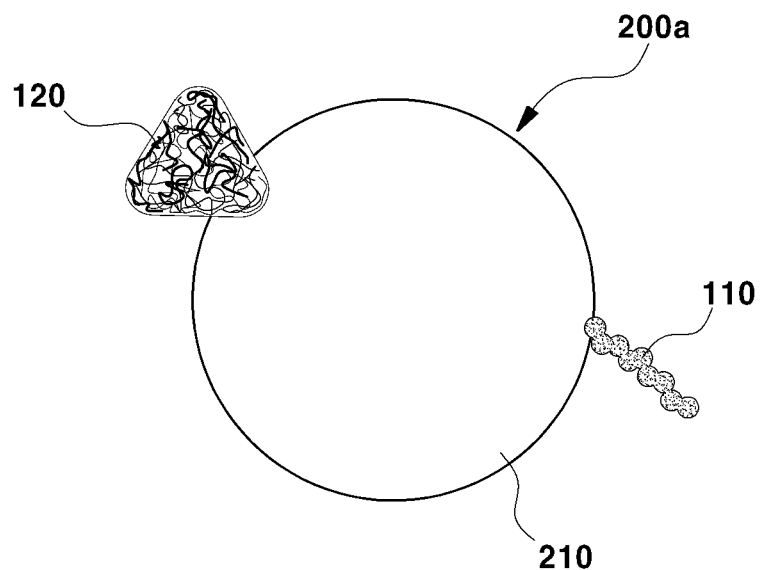
FIG. 4A is a diagram showing a pharmaceutical composition 200a for treating gout according to an embodiment of the present invention including a support 210; a probe 110 coupled to the support 210; and a first enzyme 120.
Figure 4B:
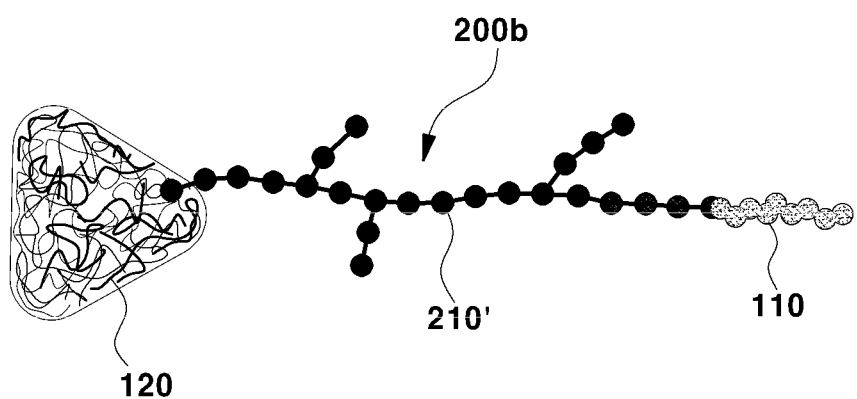
FIG. 4B is a diagram showing a pharmaceutical composition for treating gout according to another embodiment of the present invention.
Figure 4C:
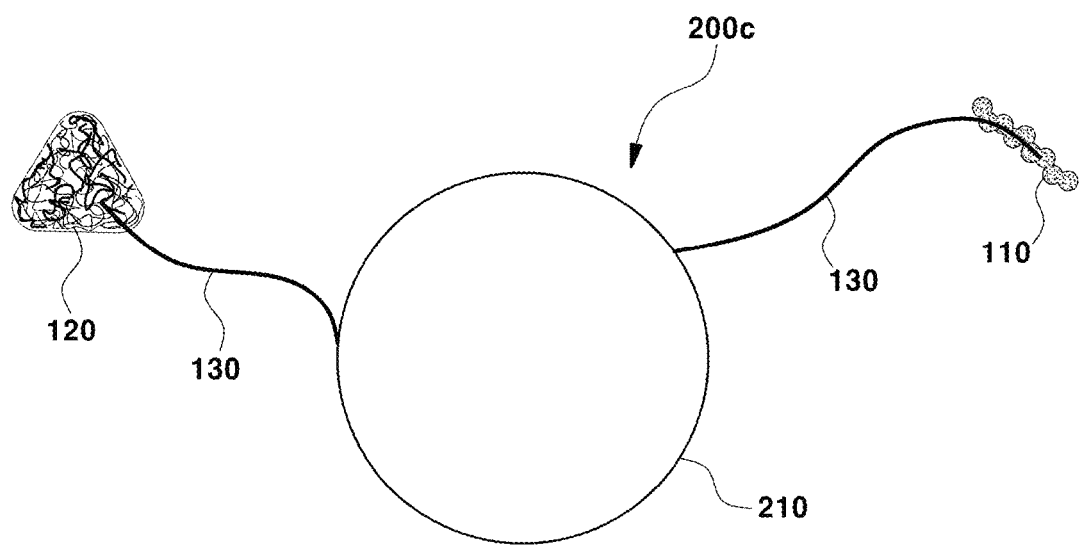
FIG. 4C is a diagram showing a pharmaceutical composition for treating gout according to another embodiment of the present invention.
Figure 4D:
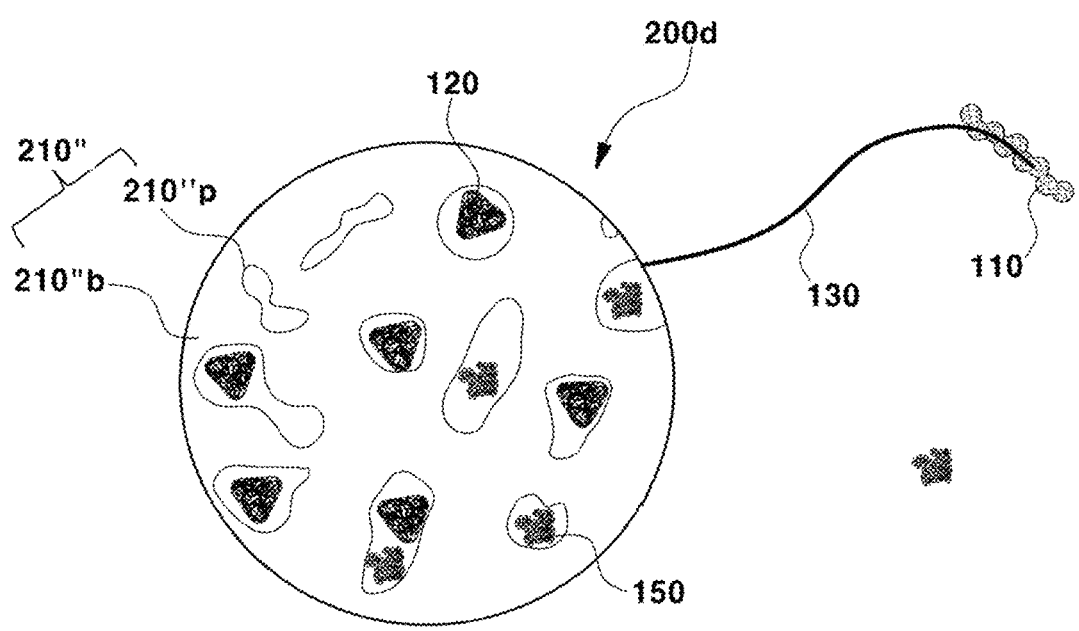
FIG. 4D is a cross-sectional diagram of the pharmaceutical composition for treating gout according to another embodiment of the present invention.

Referring to FIG. 4A, the pharmaceutical composition 200a for treating gout according to an embodiment may include a support 210; a probe 110 coupled to the support 210 and including at least one or more peptides specifically coupling to monosodium urate (MSU) crystals; and a first enzyme 120 which is coupled to and fixed to another part of the support 210, and the first enzyme 120 reacts with the target MSU crystal 10 or urea of the surrounding joint fluid to remove the target MSU crystal 10. The disclosure of pharmaceutical composition 100a~100c for the gout treatment may be referred to the pharmaceutical composition 200a~200d for the gout treatment if there are no contradictions, and references in the opposite direction may also be identically applied.

The first enzyme 120 and/or the probe 110 may be a protein in which an amino acid chain forms a three-dimensional structure, and some structures of the first enzyme 120 in the three-dimensional structure may react with the target MSU 10, or urea, and some structures of the probe 110 may specifically react with the target MSU crystal 10. Further, some structures of the probe 110 may specifically react with the target MSU crystal 10. The three-dimensional structure may be formed by an intermolecular bond such as a hydrogen bond and a van der Waals bond, and the intermolecular bond may be modified according to the surrounding pH or temperature. In an embodiment of the present invention, the first enzyme 120 and the probe 110 are fixed to the support 210 by the intermolecular bond, thereby maintaining stably the three-dimensional structure so that the functions of the first enzyme 120 and/or the probe 110 may be sustainable, even if the pH of the surrounding joint fluid is changed by the action of the first enzyme 120, or even if the ambient temperature changes by introduction of the pharmaceutical composition 200a into the living body.

In one embodiment, the support 210 may be a solid particulate structure. The particulate structure may be spherical, such as s microbead, or may be a hydrogel having a variable shape. The particulate structure may include a bio-compatible substance such as gold or platinum. In other embodiments, the support 210 may be a plate-like structure, a linear structure, a chain structure, a network structure, or a combination thereof, and may be a structure having at least some angled corners and other rounded corners. The structure of the support 210 is not limited to a specific structure, and the above examples do not limit the present invention.

Referring to FIG. 4B, in one embodiment, the support 210' may be a branched structure. The branched structure may be a polymer formed by a polymerization reaction of a unit. The branched structure may be a chain structure having a plurality of branches. The branched structure may have a length that is considerably longer than that of the first enzyme 120 and/or the probe 110, for example, 10 to $10^3$ times. According to an embodiment of the present invention, the degree of freedom that the probe 110 may move in a region around the first enzyme 120 may be improved by the branched structure, and thus, the probe 110 may be combined with the target MSU crystal 10 with a high probability to provide a highly effective gout treatment pharmaceutical composition.

Referring to FIG. 4c, in one embodiment, the support 210 and the first enzyme 120 may be coupled and fixed to each other via a linker 130 as a medium, and the probe 110 may be coupled to and fixed to the support 210 via other linker 130 used as a medium. For a detailed description of the linker 130, reference may be made to the disclosure of FIG. 2 if there are no contradictions.

Referring to FIG. 4D, in one embodiment, the support 210" may include a porous structure. FIG. 4D is a diagram showing a cross section of the support 210". The support 210" includes at least one or more cavity 210"p, and the periphery of the cavity 210"p is surrounded by a body 210"b. The first enzyme 120 and/or the second enzyme 150 may be deposited in the cavity 210"p and accommodated in the support 210". Some of the cavity 210"p may be open pores connected to the outside of the support 210", and other parts of the cavity 210"p may be closed pores.

The support 210" may be a particulate structure having a plurality of cavities, a hydrogel having a variable shape, a plate-shaped structure, or a structure having at least some angled corners and other rounded corners. The first enzyme 120 may be accommodated in the plurality of the cavities, and the probe 110 may be attached to the outside of the porous structure. In another embodiment, the probe 110 may be coupled to the porous structure through the linker 130.

The porous structure may be a porous microbead made of a biocompatible substance such as gold or platinum.

In one embodiment, the support 210 and the first enzyme 120 and/or the support 210 and the probe 110 may be coupled by a covalent bond or an ionic bond. In other embodiments, they may be coupled by attaching the same or different chemical functional groups to both ends. The detailed description of the coupling between the support 210 and the first enzyme 120 and/or the support 210 and the probe 110 may refer to the disclosure about the coupling between the first enzyme 120 and linker 130 and/or the probe 110 and the linker 130 in FIG. 2 if there are no inconsistencies.

In one embodiment, the support 210 may include one or more selected from a biodegradable substances such as a biocompatible inorganic substance or collagen, hyaluronic acid, chitosan, gelatin, polysaccharides, polylactic acid (PLA), polyglycolide JPGA) or polylactic acid-glycolide (PLGA). The support 210 may include a copolymer of polylactic acid and polyglycolide (PLGA). When the support 210 is formed of a biocompatible inorganic substance, for example, gold or platinum, an immune rejection reaction or an inflammatory reaction may not occur even if the support 210 is not decomposed in vivo. In addition, when the support 210 is formed of the biodegradable substance, as it is decomposed and removed after a predetermined time, it may be used continuously without an immune rejection reaction. Further, the first enzyme 120 and the probe 110 may be supported in a fixed manner for a considerable time during which the MSU crystal may be dissolved since it is maintained for the predetermined time.

In one embodiment, the probe 110 and the first enzyme 120 are coupled to the support 210 and, accordingly, fixed to the support 210, and a second enzyme 150 for removing the occupying protein adsorbed on the target MSU crystal 10 may be additionally coupled to the support 210 and, accordingly fixed to the support 210. The second enzyme 150 may be coupled to the support 210 via the linker 130. As for a detailed description of the coupling between the second enzyme 150 and the linker 130, reference may be made to the disclosure regarding the probe 110, the first enzyme 120, and the linker 130 in a range of that there are no contradictions.

In one embodiment, the pharmaceutical compositions 200a-18 200d for treating gout may further include a decomposition accelerator that increases the biodegradation rate of the support 210 or conversely a decomposition retarding agent that decreases the biodegradation rate of the support 210. The decomposition accelerator may include a hydrophilic compound. For example, the decomposition accelerator may be a physiologically inert water-soluble polymer such as low molecular weight methyl cellulose or hydropropyl methyl cellulose, or monosaccharides such as fructose and glucose, disaccharides such as lactose and sucrose, and polysaccharides such as cellulose, amylose, and dextrin. The accelerator may contain any substance that is hydrophilic, and at least a part may include particles such as powder or fine particles made of a hydrophilic polymer.

The decomposition retarding agent may include a hydrophobic compound to reduce the biodegradation rate. For example, the decomposition retarding agent may include a water-insoluble polymer such as high molecular weight methyl cellulose and ethyl cellulose, and a low water-soluble organic compound. The decomposition retarding agent may include any hydrophobic substance, and at least a portion may include powder or fine particles made of a hydrophobic polymer.

By controlling the biodegradation rate of the support 210 by adjusting the added amount of the decomposition accelerator or the decomposition retarding agent, the dwell time of the support 210 may be sufficiently ensured to decompose the MSU crystal. In addition, after the MSU crystal is reduced to less than a predetermined value, the support 210 may be decomposed to prevent occurrence of an immune rejection reaction in vivo. Since the amount of each patient's MSU crystal is different, the added amount of the decomposition accelerator or the decomposition retarding agent may be adjusted according to the amount of the MSU crystal.

According to another embodiment, the biodegradation rate of the support 210 may vary depending on the structure of the support 210. For example, when the support 210 has a spherical structure such as a micro bead and accordingly the surface area per unit volume of the support 210 is small, the biodegradation rate of the support 210 may be slow. On the other hand, when the support 210 has a large surface area per unit volume thereof, for example, a network structure or a porous structure, compared to the spherical structure, the biodegradation rate of the support 210 may be high. When a component of the support 210 is a material capable of forming various structures such as a polymer structure, the biodegradation rate may be controlled by modifying the structure of the support 210.

In one embodiment, the support 210 may have photoreactivity or chemical reactivity. For example, a color developing material, a light emitting substance, a fluorescent substance, or a combination thereof may be included. The fluorescent material may include a FAM fluorescent substance or a TAMRA fluorescent substance. However, the above-described substances are only examples, and the substances that cause optical reactions such as fluorescence, light emission, and color development, chemical reactions, or electrical reactions may be applied without limitation. In this case, the pharmaceutical composition 200a~200d for treating gout is administered by causing a corresponding optical reaction, chemical reaction, or electrical reaction in a state that the support 210 is coupled with the probe 110 or in a state that the support 210 is coupled with the probe 110 through the linker 130. After a predetermined time has elapsed, the amount of MSU crystals remaining in the joint fluid may be quantified by extracting the patient's joint fluid and then quantifying the optical, chemical or electrical response of the extracted joint fluid.

In one embodiment, the pharmaceutical composition 100, 200 for treating gout may further include a third enzyme (not shown) that decomposes a protein in the joint fluid containing the target MSU crystal 10. The joint fluid is highly viscous due to a high concentration of hyaluronic acid, so it may be preferable that the hyaluronic acid and other substance in the body are decomposed by the decomposing enzyme for precise diagnosis. For example, the digestive enzyme may include a protease such as hyaluronidase or proteinase K.

Figure 5:
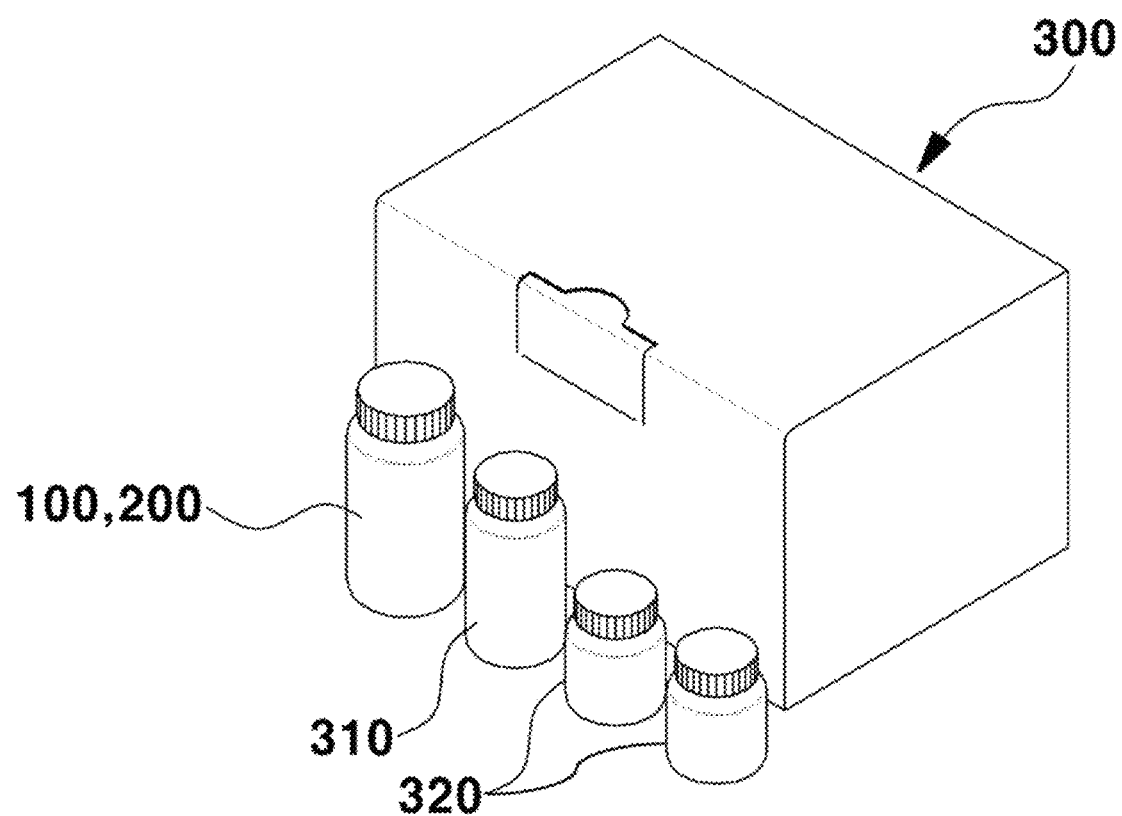
FIG. 5 is a diagram showing a kit for treating gout according to an embodiment of the present invention.

FIG. 5 is a diagram showing a gout treatment kit 300 according to an embodiment of the present invention.

In one embodiment, the gout treatment kit 300 may include a pharmaceutical composition 100, 200 for treating gout comprising a probe 110 including at least one or more peptides selectively reacting with monosodium urate MSU crystals; and a first enzyme 120 which is coupled to the probe 110, and reacts with the target MSU crystal 10 coupled to the probe 110 or urea of the surrounding joint fluid to dissolve the target MSU crystal. In addition, the gout treatment kit 300 may further include a gout diagnosis probe 310 or may further include sample plated 320 for mass spectrometry. The gout treatment kit 300 may be a pharmaceutical pack or kit including a pharmaceutical composition 100, 200 for treating gout. Optionally, the kit may further include a guide document determined by a government agency for regulating the manufacture, use, or sale of pharmaceuticals or biological products.

In another embodiment, the gout treatment kit 300 may be a kit consisting of a pharmaceutical composition 100 and 200 for treating gout, and a gout diagnostic probe 310, or a pharmaceutical composition for treating gout and a sample plate 320 for a mass spectrometry. The sample plate 320 for mass spectrometry 320 is not limited to a specific shape as long as the sample plate 320 may function as a reaction region in which an analyte solution may be provided. The sample plate 320 may include all kinds of containers such as a plurality of wells, cells, and substrate 321, a cell pellet, or a plate and may include materials such as glass, plastic, and polymer.

Figure 6A:
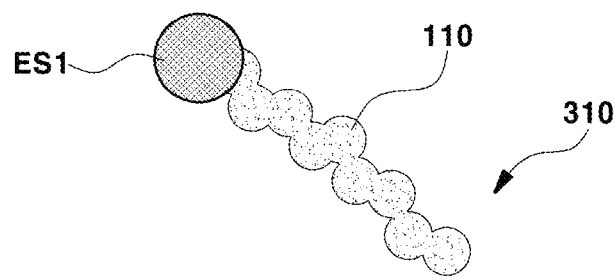
FIG. 6A is a diagram showing a probe for diagnosing gout according to an embodiment of the present invention.
Figure 6B:
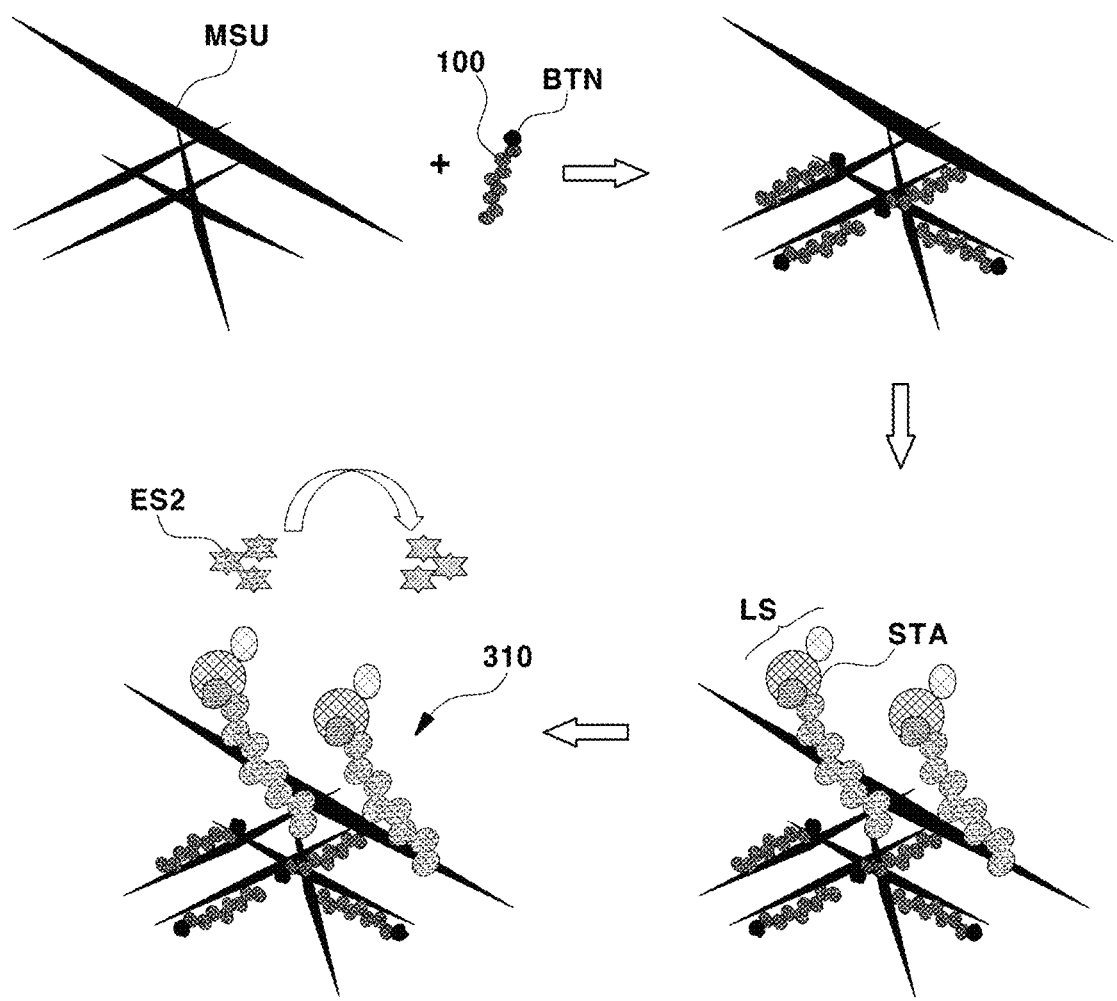
FIG. 6B is a diagram showing a probe for diagnosing gout according to another embodiment of the present invention.

FIG. 6A is a diagram showing a gout diagnosis probe 310 according to an embodiment of the present invention, and FIG. 6B is a diagram showing a gout diagnosis probe 310 according to another embodiment of the present invention.

Referring to FIG. 6A, in one embodiment, the gout diagnosis probe 310 includes a peptide that is coupled to at least one or more first expression substrate ES1, and the first expression substrate ES1 may include a chromogenic substance, a luminescent substance, and fluorescent substances or combinations thereof. The fluorescent substance may include a FAM fluorescent substance or a TAMRA fluorescent substance. However, the above-described substances are only examples, and substances that cause optical reactions such as fluorescence, light emission, and color development, chemical reactions, or electrical reactions may be applied without limitation. After extracting the joint fluid from the patient and reacting the gout diagnosis probe 310 with the extracted joint fluid, the presence and amount of MSU crystals may be measured by observing the color reaction, luminescence reaction, or fluorescence reaction. When the MSU crystal is present in a predetermined amount or more, a pharmaceutical composition 100, 200 for treating gout may be administered to the patient, and instructions for the predetermined amount may be described in the guide document.

The peptide may include at least one or more of an amino acid sequence of SEQ ID NO: 1-SEQ ID NO: 5. The peptide may have reactivity specifically coupling to MSU crystals. Detailed description of the peptide may refer to the disclosure regarding the peptide of FIG. 1.

Referring to FIG. 6B, in another embodiment, the gout diagnosis probe 310 may include a peptide coupled to at least one or more labeling substance LS. The labeling substance LS causes at least one or more of optical, electrical or chemical variation of the secondary expression substrate ES2 by a catalytic reaction, and the secondary expression substrate ES2 may include a chromogenic substance, a luminescent substance, a fluorescent substance, or a combination thereof.

In one embodiment, the peptide may include a coupling portion for coupling with the labeling substance LS. For example, the peptide is biotinylated with biotin BTN, and since the biotin BTN coupled to the peptide may serve as a coupling portion, it may be coupled to the labeling substance LS via the biotin BTN. The labeling substance LS may be horseradish peroxidase HRP to which streptavidin STA is coupled. Biotin BTN has high affinity with streptavidin STA or avidin and thus, may be used for bio-analysis using the peptide or protein molecule.

When extracting the patient's joint fluid to provide the gout diagnosis probe 310, the gout diagnosis probe 310 may be coupled to the MSU crystal by the peptide. Thereafter, the gout diagnosis probe 310 that is not coupled to the MSU crystal may be removed. For example, a washing process may be used. The labeling substance LS coupled to the peptide may remain in the reaction region even after the washing process, and when the secondary expression substrate ES2 is provided in the reaction region, a catalytic reaction of the labeling substance LS may occur, and the catalytic reaction may be proportional to the concentration of MSU crystals in the patient's joint fluid.

The labeling substance LS may cause at least one or more of optical, electrical, or chemical variations of the secondary expression substrate ES2 by catalytic reaction. For example, in one embodiment, the labeling substance LS may include horseradish peroxidase HRP, alkaline phosphatase AP, and peroxidase compounds, to which streptavidin STA is coupled, and may include, for example, β-galactosidase, horseradish peroxidase, luciferase or cytochrome P450. Alternatively, the oxidation-reduction reaction of the secondary expression substrate ES2 may occur by the catalytic reaction of the label substance LS, and the magnitude of the current generated during the oxidation-reduction reaction may be measured. The above-described substances are exemplary, and the enzymes which catalyze a color reaction, a fluorescence reaction, a luminescence reaction, or an infrared reaction, and the substances that act as the enzymes may all be applied, and are not limited to specific substances.

In another embodiment, when the labeling substance LS includes alkaline phosphatase AP, color and/or fluorescent substances including bromochloroindolyl phosphate BCIP, nitro blue tetrazolium NBT, naphthol-ASB1-phosphate, paranitrophenyl phosphate, enhanced chemifluorescence ECF, or combinations thereof may be used as a secondary expression substance.

In another embodiment, when the labeling substance LS is horseradish peroxidase, chloronaphthol, aminoethylcarbazole, diaminobenzidine, D-luciferin, and lucigenin (Bis-N-methylacridinium nitrate), resorphine benzyl ether, luminol, amplex red reagent (10-acetyl-3,7-dihydroxyphenoxazin), p-phenylenediamine-HCl and pyrocatechol (HYR), tetramethylbenzidine (TMB), ABTS (2,2'-Azine-di[3-ethylbenzthiazoline sulfonate]), o-phenylenediamine (OPD) and naphthol/pyronine, glucose oxidase and t-NBT (nitroblue tetrazolium), m-PMS (phenzaine methosulfate), or a combination of these may be used as a secondary expression substance, and the above-described substances are only examples, and any material inducing any one of optical, electrical, or chemical changes by a catalytic reaction of the label substance LS may be applied, and it is not limited to the specific substances.

The gout treatment kit 300 according to an embodiment may further include an assay kit for quantifying MSU crystals using the gout diagnosis probe 310, and the assay kit may be an immunoassay kit. For example, the gout treatment kit 300 may be a luminex assay kit, a protein microarray kit, or an ELISA kit. Various embodiments include radioimmunoassay, radioimmunoprecipitation, immunoprecipitation, immunohistochemical staining, ELISA, capture-ELISA, inhibition or hardwood analysis, sandwich analysis, flow cytometry, immunofluorescence staining, and immunoaffinity purification, but is not limited to them. A description of a commercially available assay method may be applied to the kits for immunoassay.

In one embodiment, the optical variation of the secondary expression substrate ES2 may include a light emission reaction, a color development reaction, or a fluorescence reaction, and the assay kit may quantify the optical variation. In another embodiment, the electrical variation may be quantified by an ammeter, a voltmeter, chronoamperometry, or chronoovoltametry. For example, when the secondary expression substrate ES2 is TMB, an oxidation-reduction reaction may be caused by the labeling substance LS, and an electron transfer may occur for the oxidation-reduction reaction. When an electric signal is generated at the reaction region due to the electron transfer, the MSU crystals may be quantified by measuring the magnitude of the electric signal.

Figure 7:
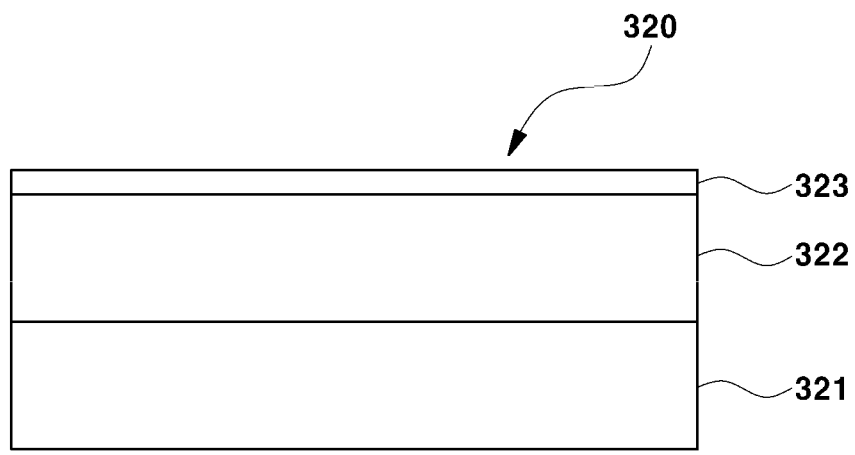
FIG. 7 is a diagram showing a sample plate for mass spectrometry according to an embodiment of the present invention.

FIG. 7 is a diagram showing a sample plate 320 for mass spectrometry according to an embodiment of the present invention.

Referring to FIG. 7, in one embodiment, the gout treatment kit 300 may further include a sample plate 320 for mass spectrometry. The sample plate may include a substrate 321 and a matrix layer 322, and may include an analyte layer 323 formed from an analyte crystal. In one embodiment, the substrate 321 may include metal atoms, some or all of which make up the matrix layer 322. For example, when the matrix layer 322 includes a metal oxide, the surface or the entire surface of the substrate 321 may include a metal of the metal oxide, and the surface of the substrate 321 may be oxidized to form the matrix layer 322. In one embodiment, the substrate 321 is a titanium plate (Ti plate), may include tantalum Ta, tin Sn, tungsten W, zinc Zn, vanadium V, ruthenium Ru, iridium Ir, iron Fe, stainless steel) or alloys thereof. In the case of the titanium Ti oxide, there are advantages that the price is relatively low, the supply is smooth, there is no photocorrosion property, and the efficiency of the photolysis reaction is increased due to a low band gap, 3.2 eV. However, the constituent elements of the substrate 321 are not limited to the aforementioned substances.

In one embodiment, the matrix layer 322 is formed by nanostructures, the nanostructures may be any one of nanoparticle structures, nanowire structures and composite nanostructures having the nanowires and nano particle coated on the nanowires (hereinafter, referred to as 'composite nanostructures'). In one embodiment of the present invention, the matrix layer 322 may be formed by any one of a nanoparticle structure containing $TiO_2$, a nanowire structure containing $TiO_2$, and a composite nanostructure coated with $TiO_2$ nanoparticles on the nanowire containing $TiO_2$. A porous structure of the nanostructures may facilitate ionization and desorption of an analyte, and thus may be suitable for an analyte having a small molecular size. In addition, the nanostructures may have a fiber shape, a wire shape, a needle shape, a rod shape, a column shape, or a combination of these.

An analyte crystal may be formed according to a method wherein the joint fluid of a patient is extracted and the joint fluid is reacted with a proteolytic enzyme to decompose a substance inside the joint fluid, and then the decomposed joint fluid is filtered through a microfiltration membrane so that the crystals remaining on the microfiltration membrane may be dissolved in a solvent. In one embodiment of the invention, in connection with the microfiltration membrane, a membrane filter having a pore size of a 0.1 μm (polytetrafluoroethylene (PTFE) of a pore size 0) may be used. Thereafter, the crystal solution in which the crystal is dissolved may be crystallized on a sample plate. Subsequently, after the crystal solution is crystallized on the sample plate to form the analyte layer 323, the mass peak of the MSU crystal may be measured by performing a MALDI-TOF MS (Matrix assisted laser desorption/ionization time-of-flight mass spectrometry).

In one embodiment, MSU crystals may be quantified by means of a matrix assisted laser desorption/ionization time-of-flight mass spectrometry (MALDI-TOF MS) using a sample plate 320 for mass spectrometry. First, an analyte layer 323 may be formed on the matrix layer 322 as described above. In general, in one embodiment, a solution in which the analyte and the nanostructures are mixed may be dropped on a target metal plate, or a solution containing the analyte may be dropped on a substrate 321 on which the matrix layer 322 is formed. Thereafter, the analyte or a solution in which the analyte and the nanostructures are mixed, may be dried to form an analyte layer 323.

In one embodiment, the diameter of the nanoparticles containing $TiO_2$ may be 16 nm to 25 nm. In addition, the diameter of the nanoparticles containing $TiO_2$ effective for ionization and desorption in MALDI-TOF MS may vary depending on the type of sample, the nature of the solution, the type of metal, and the type of nanostructure. In addition, in one embodiment, according to XRD imaging results, the nanoparticles containing $TiO_2$ may have a crystal structure of rutile, anatase, or a mixed crystal structure thereof.

In another embodiment, the nanowire containing $TiO_2$ may have a mesh structure, the average size of pores of the mesh structure may be 80 nm to 300 nm, and the diameter of the nanowire containing $TiO_2$ may be 25 nm to 35 nm. In addition, in one embodiment, the TiRD peak may be observed as a result of XRD imaging of the nanowires containing $TiO_2$, and may have a rutile crystal structure, an anatase crystal structure, a layered crystal structure or a mixed crystal structure thereof. Preferably, it may have an anatase crystal structure. In MALDI-TOF MS, the photocatalytic reaction of the sample plate 100 depends on the electron-hole recombination ratio, which is influenced by charge separation and trapping at the interface. The nanoparticles containing $TiO_2$ and the nanowires containing $TiO_2$ have various crystal structures. Further, thanks to the interface of the various crystal structures, the recombination ratio of the electron-holes is reduced and as a result, an efficient photocatalytic action of the sample plate 320 may be expected.

In another embodiment, the composite nanostructure may be formed by coating the nanoparticles containing $TiO_2$ on the nanowire containing $TiO_2$. The composite nanostructure has the advantage of having a large area in contact with the analyte. In addition, the $TiO_2$ nanoparticles may be evenly distributed or aggregated on the nanowires containing $TiO_2$, and the aggregation phenomenon varies depending on the size or concentration of the nanoparticles containing $TiO_2$. Further, in order to obtain an optimal mass peak, the size or the concentration of the nanoparticles may be adjusted.

According to an embodiment of the present invention, the gout treatment kit 300 may preemptively quantify MSU crystals in the patient's joint fluid by using the gout diagnosis probe 310 or the mass spectrometer sample plate 320. Therefore, the presence and/or amount of MSU crystals may be measured by a simple method, and a pharmaceutical composition for treating gout at a dose or concentration suitable for the amount of MSU crystals may be injected. In addition, when quantifying the MSU crystal by using the gout diagnosis probe 310 or the mass spectrometer sample plate 320, it is possible to quantify by using only a very small amount of joint fluid, and thus, a preemptive diagnosis that does not burden the patient may be possible.

In one embodiment, the pharmaceutical composition kit for treating gout may be a smart kit. For example, the pharmaceutical composition 100, 200 for treating gout may be an implant device that may be inserted into a joint in which MSU crystals are present. Alternatively, it may be a patch using a microneedle that may inject the pharmaceutical composition 100, 200 for treating gout into the joint. For example, a drug delivery system that may be screwed to a patient's joint and spread the pharmaceutical compositions 100, 200 for treating gout at a predetermined rate around the joint may be used. Further, it may be a device wherein a micro-scale needle is filled in advance with a pharmaceutical composition 100, 200 for treating gout, and the composition is discharged by a repulsive force, or may be a drug patch using various current injection tools. The smart kit may control a release amount of a pharmaceutical composition for treating gout via a wireless communication from the outside, or set a predetermined release ratio so that a predetermined amount may be released per hour. According to an embodiment of the present invention, in the case of a chronic gout patient in which gout attacks occur periodically, continuous dissolution of MSU crystals may be realized even without periodically injecting a pharmaceutical composition for treating gout by applying the smart kit to a human body.

It will be clear to those having a common knowledge in the technical field to which the present invention pertains that the present invention described above is not limited to the above-described embodiments and the accompanying drawings, and various substitutions, modifications, and changes are possible within the scope of the present invention.

EXPLANATION OF SYMBOLS

10: a target MSU crystal
100: a pharmaceutical composition for treating gout
110: a probe
120: a first enzyme
130: a linker
140: a biodegradable support
150: a second enzyme
200: a pharmaceutical composition for treating gout
210: a support
300: a gout treatment kit
310: a gout diagnosis probe
ES1: a first expression substrate
LS: a labeling substance
ES2: a secondary expression substrate
320: a sample plate for mass spectrometry,
321: a substrate
322: a matrix layer
323: an analyte layer

What is claimed is:

1. A pharmaceutical composition for treating gout comprising,
   a probe containing at least one or more peptides specifically coupling to monosodium urate (MSU) crystals; and
   a first enzyme which reacts with a target MSU crystal coupled to the probe or urea of surrounding joint fluid to remove the target MSU crystal,
   wherein the at least one or more peptides are selected from the group consisting of SEQ ID NO: 1 to SEQ ID NO: 5, and
   wherein the first enzyme is selected from the group consisting of uricase, rasburicase, and urease.

2. The pharmaceutical composition for treating gout of the claim 1, wherein the first enzyme generates ammonium ions in the surrounding joint fluid to raise the pH of the surrounding joint fluid, thereby dissolving and removing the target MSU crystal.

3. The pharmaceutical composition for treating gout of the claim 1, wherein the first enzyme oxidizes the target MSU crystal coupled to the probe or urea of the surrounding joint fluid to decompose and remove the target MSU crystal.

4. The pharmaceutical composition for treating gout of the claim 1, wherein the first enzyme is selected from human-derived substances so as not to cause an immune rejection reaction in a human body.

5. The pharmaceutical composition for treating gout of the claim 1, further comprising a linker coupled between the probe and the first enzyme to provide a predetermined degree of freedom to the probe.

6. The pharmaceutical composition for treating gout of the claim 1, further comprising a second enzyme which removes an occupying protein adsorbed on the target MSU crystal.

7. The pharmaceutical composition for treating gout of the claim 1, further comprising a biodegradable support for carrying a cluster of a unit composition formed by combining the first enzyme and the probe, and is maintained as a limited level for a predetermined period in vivo.

8. The pharmaceutical composition for treating gout of the claim 7, further comprising a second enzyme which removes an occupying protein adsorbed on the target MSU crystal, and wherein the biodegradable support contains the second enzyme.

9. A pharmaceutical composition for treating gout comprising, a support;
   a probe including at least one or more peptides which are coupled to and fixed to a portion of the support, and specifically coupled to monosodium urate, (MSU) crystals; and
   a first enzyme which is coupled to and fixed to other portion of the support, and reacts with a target MSU crystal coupled to the probe or urea of the surrounding joint fluid to remove the target MSU crystal,
   wherein the at least one or more peptides are selected from the group consisting of SEQ ID NO: 1 to SEQ ID NO: 5, and
   wherein the first enzyme is selected from the group consisting of uricase, rasburicase, and urease.

10. The pharmaceutical composition for treating gout of the claim 9, further comprising a linker coupled between the support and the probe to provide a predetermined degree of freedom to the probe.

11. The pharmaceutical composition for treating gout of the claim 9, wherein the first enzyme decomposes and then removes the target MSU crystal by oxidizing the target MSU crystal coupled to the probe or urea of the surrounding joint fluid.

12. The pharmaceutical composition for treating gout of the claim 9, wherein the support includes one or more of biocompatible inorganic substance, collagen, hyaluronic acid, chitosan, gelatin, polysaccharides, polylactic acid (PLA), or polyglycolide (PGA).

13. The pharmaceutical composition for treating gout of the claim 9, further comprising a decomposition accelerator for increasing a biodegradation rate of the support or a decomposition retarding agent for reducing the biodegradation rate of the support.

14. The pharmaceutical composition for treating gout of the claim 9, wherein the support includes a color developing substance, a light emitting substance, a fluorescent substance, or a combination thereof.

15. A gout treatment kit including a pharmaceutical composition comprising,
   a probe containing at least one or more peptides selectively reacting with monosodium urate MSU crystals; and a first enzyme which reacts with the target (MSU) crystal coupled to the probe, or urea of the surrounding joint fluid to remove the target MSU crystal, wherein the at least one or more peptides are selected from the group consisting of SEQ ID NO: 1 to SEQ ID NO: 5, and wherein the first enzyme is selected from the group consisting of uricase, rasburicase, and urease.

16. The gout treatment kit of the claim 15, further comprising a gout diagnosis probe and a secondary expression substrate, and wherein the gout diagnosis probe includes a peptide coupled to at least one or more labeling substances or at least one or more first expression substrates, wherein the labeling substance may cause at least one or more of optical variation, electrical variation, or chemical variation of the secondary expression substrate by a catalytic reaction, and wherein the first or the secondary expression substrates include a color developing substance, a light emitting substance, a fluorescent substance, or a combination thereof.

17. The gout treatment kit of the claim 15, further comprising a sample plate for mass spectrometry, and wherein the sample plate includes the matrix layer formed by any one of a nanoparticle structure containing $TiO_2$, a nanowire structure containing $TiO_2$, and a composite nanostructure coated with the $TiO_2$ nanoparticles on the nanowire containing $TiO_2$.

* * * * *

SEQUENCE LISTING

<160> NUMBER OF SEQ ID NOS: 5

<210> SEQ ID NO 1
<211> LENGTH: 15
<212> TYPE: PRT
<213> ORGANISM: Artificial Sequence
<220> FEATURE:
<223> OTHER INFORMATION: Synthesized

<400> SEQUENCE: 1

Ala Arg Gly Val Asn Pro Gly Ile Met Gly Arg Asp Tyr Trp Gly
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthesized

<400> SEQUENCE: 2

Ala Arg Tyr Ala Gly Ser Leu Glu Ser Gly Ala Asp Asp Trp Gly
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthesized

<400> SEQUENCE: 3

Ala Arg Cys Glu Ser Gly Arg Pro Gly Ser Val Asp Phe Trp Gly
1               5                   10                  15

<210> SEQ ID NO 4

```
<211> LENGTH: 15
<212> TYPE: PRT
<213> ORGANISM: Artificial Sequence
<220> FEATURE:
<223> OTHER INFORMATION: Synthesized

<400> SEQUENCE: 4

Ala Arg Cys Leu Glu Leu Leu Gly Arg Lys Ile Asp Phe Trp Gly
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthesized

<400> SEQUENCE: 5

Ala Arg Cys Leu Glu Leu Leu Gly Arg Lys Ile Asp Phe Trp Gly
1               5                   10                  15
```